US008383145B2

(12) United States Patent
Asari et al.

(10) Patent No.: US 8,383,145 B2
(45) Date of Patent: Feb. 26, 2013

(54) FILM-FORM PREPARATION (75) Inventors: Daisuke Asari, Ibaraki (JP); Mitsuhiko Hori, Ibaraki (JP); Takuya Shishido, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/014,245

(22) Filed: Jan. 26, 2011

(65) Prior Publication Data
US 2011/0182993 A1 Jul. 28, 2011

(51) Int. Cl.
*A61K 48/00* (2006.01)

(52) U.S. Cl. .......................................... 424/439; 424/443

(58) Field of Classification Search .................. None
See application file for complete search history.

(56) References Cited

U.S. PATENT DOCUMENTS

| 4,687,660 | A * | 8/1987 | Baker et al. | 424/465 |
| 2005/0147653 | A1 | 7/2005 | Yasuda et al. | |
| 2007/0237871 | A1 | 10/2007 | Furusawa | |
| 2009/0155351 | A1 | 6/2009 | Hejl et al. | |
| 2011/0293720 | A1* | 12/2011 | General et al. | 424/485 |

FOREIGN PATENT DOCUMENTS

| JP | 2004-43450 A | 2/2004 |
| JP | 2005-511522 | 4/2005 |
| JP | 2005-511522 A | 4/2005 |
| JP | 2006-513269 | 4/2006 |
| JP | 2006-513269 A | 4/2006 |
| JP | 2007-500252 | 1/2007 |
| JP | 2007-500252 A | 1/2007 |
| JP | 2009-507854 | 2/2009 |
| JP | 2009-507854 A | 2/2009 |
| JP | 2009-510136 | 3/2009 |
| JP | 2009-510136 A | 3/2009 |
| WO | 03/030882 A1 | 4/2003 |
| WO | 2004/047794 A2 | 6/2004 |
| WO | 2005/039499 A2 | 5/2005 |
| WO | WO 2005039499 A2 * | 5/2005 |
| WO | 2006/031209 A1 | 3/2006 |
| WO | 2007/030754 A2 | 3/2007 |
| WO | 2007/038926 A1 | 4/2007 |
| WO | 2010/086989 A1 | 8/2010 |

OTHER PUBLICATIONS

Extended European Search Report for corresponding European Application No. 11000618.6, dated Apr. 20, 2011.
European Office Action issued in Application No. 11000618.6 dated Nov. 2, 2012.

* cited by examiner

*Primary Examiner* — Anand Desai
*Assistant Examiner* — Melissa Mercier
(74) *Attorney, Agent, or Firm* — Sughrue Mion, PLLC (57) ABSTRACT

An object of the present invention is to provide a film-form preparation to be used in desensitization therapy and a method for producing the same. This film-form preparation enables the patient to self-administer an allergen and adjust the dose, has excellent portability, has no residual sensation, provides excellent protection against accidental swallowing, is easy for a caregiver to administer, and can greatly improve the QOL of both patients and caregivers. Additionally, this film-form preparation enables arbitrary control of the dissolution time in the mouth, particularly sublingually and has very little gummy sensation in the mouth and better feeling when touched by the fingers. A film-form preparation including: an allergen; an edible polymer that is soluble in both water and a polar organic solvent; and one or two or more types of particles selected from the group consisting of monosaccharide to hexasaccharide sugars and sugar alcohols thereof that have an average particle size of 0.1 to 100 μm.

9 Claims, 1 Drawing Sheet

FILM-FORM PREPARATION

TECHNICAL FIELD

The present invention relates to a film-form preparation that readily dissolves in the mouth. More specifically, the present invention relates to a film-form preparation suitable for oral or sublingual administration as applied in specific desensitization therapy wherein a patient acquires immunotolerance through exposure to an allergen administered for a predetermined period of time via the mouth, e.g., oral mucosa, and particularly, the sublingual mucosa.

BACKGROUND ART

At present almost all therapy for pollen allergies and other allergic diseases consists of symptomatic treatment with antihistamines, but recently desensitization therapy has gained attention as a mode of therapy that can be completely cured cause of an allergic disease.

Because desensitization therapy generally requires long-term administration of approximately 2 to 3 years, a dosage form that will more greatly improve the quality of life (QOL) of both caregivers and patients is needed.

At present, almost all the dosage forms used in specific desensitization therapy are injectables intended for subcutaneous injection.

However, the following problems occur with specific desensitization therapy utilizing subcutaneous injections: there is a danger of anaphylactic shock, administration must be made by a healthcare provider, the patient must make frequent visits to the healthcare provider over a long period of time, there is pain associated with the injection, and the injectable preparations must be stored under refrigeration.

In contrast, liquid and tablet preparations for sublingual administration have been marketed in Europe and the United States in recent years, and they have garnered attention because they cause few adverse reactions and they are easy to use.

There have been problems with specific desensitization therapy utilizing sublingual administration of liquid preparations, however, because the dose is imprecise, the preparations require storage under refrigeration, and the like.

A solid vaccine comprising a lyophilisate comprising an oxygen-containing metal salt, an antigen, and one or more excipients selected from saccharides, sugar alcohols, and amino acids or pharmaceutically acceptable salts thereof (Japanese Translation of PCT Application No. 2009-510136), and a fast-dispersing, non-compressed solid dosage form comprising a matrix and at least one allergen (Japanese Translation of PCT Application No. 2006-513269), etc., have been proposed as a tablet or other solid preparation containing an allergen.

There have been problems with specific desensitization therapy utilizing sublingual administration of a tablet, however, because the patient can swallow the tablet by mistake, it is difficult to fine-tune the dose, the portability is poor, the residue causes an unpleasant sensation in the mouth, and the like.

Therefore, one option that comes to mind as a method to address these problems is a film-form preparation that readily dissolves in the mouth.

A film-form preparation containing allergen wherein an active substance such as an allergen is dispersed or dissolved in a water-soluble polymer are already known. Examples include a film with non-self-aggregating uniform heterogeneity and method for preparing the same (Japanese Translation of PCT Application No. 2005-511522); a fast-dissolving film free of added plasticizer that contains at least one type of water-soluble polymer comprising polyethylene oxide alone or in combination with a hydrophilic cellulose polymer (Japanese Translation of PCT Application No. 2007-500252); and an autonomous, edible film for delivery of an active ingredient comprising an edible, water-soluble polymer, an anti-tacking agent, and an active substance (Japanese Translation of PCT Application No. 2009-507854).

A film-form preparation containing an allergen needs to have very little gummy sensation when placed in the mouth and very little sticky sensation when touched by the fingers.

As methods for reducing the gummy sensation and sticky sensation, a film-form preparation wherein a non-reducing sugar and a sugar alcohol are formulated thereinto is already known, and previous film-form preparation referred to allergens, wherein a non-reducing sugar and a sugar alcohol are formulated thereinto has been reported.

However, previous film-form preparations are those wherein the active substance such as an allergen are dispersed or dissolved in a water-soluble polymer. Therefore, water or a mixture thereof is used as the solvent in the manufacturing process, and the added sugars and sugar alcohols are in a dissolved or recrystallized state in the manufactured film-form preparation.

Thus, with previous film-form preparations it has been impossible to fully satisfy the film properties related to a gummy sensation when placed in the mouth, a sticky sensation when touched by the fingers, and high film strength merely by the addition of a sugar or sugar alcohol, and particularly a large amount of sugar or sugar alcohol. In addition, previous film-form preparations have not been considered optimal for patient desensitization therapy using an allergen because it has been almost impossible to intentionally control the dissolution time in the mouth.

PRIOR ART DOCUMENT

Patent Document
  Patent Document 1: JP-T 2009-510136
  Patent Document 2: JP-T 2006-513269
  Patent Document 3: JP-T 2005-511522
  Patent Document 4: JP-T 2007-500252
  Patent Document 5: JP-T 2009-507854

SUMMARY OF THE INVENTION

Problems to be Solved by the Invention

In light of the above, an object of the present invention is to provide a film-form preparation to be used in desensitization therapy and a method for producing the same. This film-form preparation enables the patient to self-administer an allergen and adjust the dose, has excellent portability, has no residual sensation, provides excellent protection against accidental swallowing, is easy for a caregiver to administer, and can greatly improve the QOL of both patients and caregivers. Additionally, this film-form preparation enables arbitrary control of the dissolution time in the mouth, particularly sublingually, has very little gummy sensation in the mouth and very little sticky sensation when touched by the fingers (improved feel), and enables a high film strength to be obtained.

Means for Solving the Problems

After thorough and incisive investigation of the above problem, the inventors discovered that a film-form preparation prepared by dispersing a sugar or sugar alcohol as microparticles in a polymer that is soluble both in water and an organic solvent clearly has better properties than prior products, thus completing the present invention.

More specifically, the present invention is a film-form preparation including: an allergen; an edible polymer that is soluble in both water and a polar organic solvent; and one or two or more types of particles selected from the group consisting of monosaccharide to hexasaccharide sugars and sugar alcohols thereof that have an average particle size of 0.1 to 100 μm.

In the film-form preparation of the present invention, the above particles selected from the group of monosaccharide to hexasaccharide sugars and the sugar alcohols thereof preferably have an average particle size of 0.1 to 30 μm.

In addition, the above monosaccharide to hexasaccharide sugars are preferably non-reducing sugars.

Furthermore, the edible polymer that is soluble in both water and a polar organic solvent is preferably polyvinyl pyrrolidone and/or hydroxypropylcellulose.

In the film-form preparation of the present invention, the molecular weight of the above polyvinyl pyrrolidone preferably ranges from 2,500 to 3,000,000.

Moreover, the molecular weight of the hydroxypropylcellulose preferably ranges from 10,000 to 1,200,000.

The present invention is also a method for producing a film-form preparation containing: an allergen; an edible polymer that is soluble in both water and a polar organic solvent; and one or two or more types of particles selected from the group consisting of monosaccharide to hexasaccharide sugars and sugar alcohols thereof that have an average particle size of 0.1 to 100 μm, the method includes the steps of: preparing a liquid dispersion of particles obtained by adding the above allergen, the above edible polymer that is soluble in both water and a polar organic solvent, and one or two or more types of particles selected from the group consisting of monosaccharide to hexasaccharide sugars and sugar alcohols thereof that have an average particle size of 0.1 to 100 μm to a polar organic solvent; and forming and drying a thin film from the above liquid dispersion of particles.

The present invention is described in greater detail below.

Figure 1:
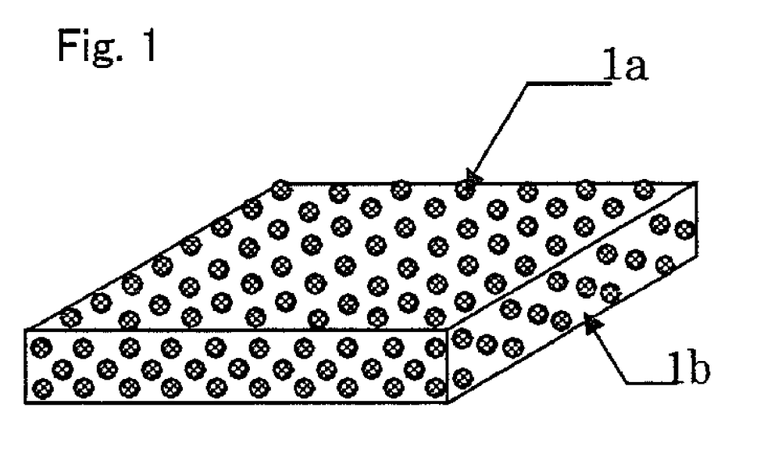
FIG. 1 is a schematic drawing showing one example of an embodiment of the film-form preparation of the present invention.

FIG. 1 is a schematic drawing showing an example of one configuration of the film-form preparation of the present invention.

As shown in FIG. 1, one or two or more types of particles 1a selected from the group consisting of monosaccharide to hexasaccharide sugars and sugar alcohols thereof that have an average particle size of 0.1 to 100 μm (hereinafter, also called "sugar or sugar alcohol particles") are dispersed in a base 1b containing the edible polymer that is soluble both in water and a polar organic solvent, and the allergen (not illustrated). As shown in FIG. 1, it is believed that the above sugar or sugar alcohol particles 1a are uniformly dispersed in the base 1b in the film-form preparation of the present invention.

The thickness of the film-form preparation of the present invention is not particularly limited herein, but a thickness of 30 to 500 μm is preferred. If the thickness is less than 30 μm, the possible problems may occur in terms of film strength and handling properties of the product, and if the thickness is greater than 500 μm, the gummy sensation in the mouth originating from the edible polymer becomes stronger, and there is concern that an unpleasant sensation may occur in the mouth.

The planar shape of the film-form preparation of the present invention is not particularly limited herein, and examples include arbitrary shapes such as rectangular, square, circle, elliptical, etc.

Examples of the above sugar or sugar alcohol particles in the film-form preparation of the present invention include the sugar or sugar alcohol particles of the monosaccharides, disaccharides, and tri- to hexasaccharides shown below.

Examples of monosaccharides include: aldotetroses such as erythrose and threose; aldopentoses such as ribose, lyxose, xylose, and arabinose; aldohexoses such as allose, talose, gulose, glucose, altrose, mannose, galactose, and idose; ketotetroses such as erythrulose; ketopentoses such as xylulose and ribulose; and ketohexoses such as psicose, fructose, sorbose, and tagatose. Examples of disaccharides include: α-diglucosides such as trehalose, kojibiose, nigerose, maltose, and isomaltose; β-diglucosides such as isotrehalose, sophorose, laminaribiose, cellobiose, and gentiobiose; α,β-diglucocides such as neotrehalose; and lactose, sucrose, and isomaltulose (palatinose). An example of a trisaccharide is raffinose, etc. Examples of tri- to hexasaccharide oligosaccharides include cyclic oligosaccharides such as fructooligosaccharides, galactooligosaccharides, xylooligosaccharides, isomaltooligosaccharides, chitin oligosaccharides, chitosan oligosaccharides, oligoglucosamine, dextrins, and cyclodextrins, etc.

Examples of monosaccharide alcohols include: tetritols such as erythritol, D-threitol, and L-threitol; pentitols such as D-arabinitol and xylitol; hexitols such as D-iditol, galactitol (dulcitol), D-glucitol (sorbitol), and mannitol; and cyclitols such as inositol. Examples of disaccharide alcohols include maltitol, lactitol, and reduced palatinose (isomalt); and examples of oligosaccharides include pentaerythritol and reduced malt sugar starch syrup.

The above sugar or sugar alcohol particles in the film-form preparation of the present invention can be optionally substituted, and one or two or more types thereof can be mixed together and used.

From the standpoint of ease of dissolution in the mouth of the film-form preparation of the present invention, the above sugar or sugar alcohol particles are preferably particles of a mono- to trisaccharide, or a sugar alcohol thereof.

Allergens are proteins and peptides. Therefore, a non-reducing sugar or sugar alcohol is preferred for the above monosaccharide to hexasaccharide sugar because it is conceivable that the antigenicity thereof will be markedly reduced by a sugar with reducing properties through a Maillard reaction.

Even more preferred as the above sugar or sugar alcohol particles in the film-form preparation of the present invention are trehalose, mannitol, xylitol, erythritol, and isomalt, which have low hygroscopicity.

The monosaccharide to hexasaccharide sugar and sugar alcohol thereof used herein has the property of being very poorly soluble in a polar organic solvent. Conversely, because the film-form preparation of the present invention contains an edible polymer described below that is soluble in both water and a polar organic solvent, a polar organic solvent can be used in the manufacture thereof. Thus, the film-form preparation of the present invention can contain the above sugar or sugar alcohol in the form of particles and also in a large amount, and a desired strength can be imparted to the film-form preparation of the present invention thereby. In previous film-form preparations an organic solvent was sometimes used during the manufacture thereof, but the organic solvent was added as a defoaming agent to eliminate bubbles generated during manufacturing, and was not for the purpose of dissolving the edible polymer.

The average particle size of the above sugar or sugar alcohol particles is 0.1 to 100 μm. If the average particle size exceeds 100 μm, the flexibility may not be uniform in some parts, and there will be a tendency for greater variance in the particle size in a film-form preparation of practical thickness, so the strength of the film-form preparation will tend to decrease (i.e., the film-form preparation will tend to become brittle). Conversely, if the average particle size is less than 0.1 µm, the particles can aggregate, and similarly the flexibility of the film-form preparation may not be uniform in some places. Even more preferably, the average particle size of the above sugar or sugar alcohol particles is 0.1 to 30 µm. By falling within this range, the sugar and sugar alcohol particles can easily be prepared into a uniformly dispersed liquid in a practical manufacturing process.

In addition, in this description the above average particle size refers to a Mass-median-diameter (D50) determined by a laser-scattering particle size distribution analyzer.

The above sugar or sugar alcohol particles can be of any shape provided they are solids, or in a contextually suitable case, aggregates thereof within the above average particle size range. A commercially available product prepared so that the above average particle size of the sugar or sugar alcohol particles lies within the above range can be used, or a commercially available product can be used after sizing so that the average particle size lies within the above range. Adjustment of the above average particle size can be carried out by pulverization or granulation using dry granulation, wet granulation, etc., classification using a sieve, mechanical classifier, etc. To easily obtain solids lying within the range for the above average particle size, the above sugar or sugar alcohol particles are preferably not obtained by a dissolution and recrystallization procedure.

The above sugar or sugar alcohol particles preferably constitute 1 to 80 wt % of the total weight of the film-form preparation of the present invention. In a film-form preparation of practical thickness, if the content is less than 1 wt %, no clear improvement is seen in the properties of rapid dissolution profile in the mouth, sufficient film strength, decrease of gummy sensation in the mouth originating in the edible polymer described below, and the sticky sensation when touched by the fingers. If the content exceeds 80 wt %, it is possible that problems with shape retention, etc., of the product will occur unless the size of the sugar or sugar alcohol particles is made very small. More preferably, the lower limit for the content of the above sugar or sugar alcohol particles is 10 wt %, and more preferably the upper limit is 60 wt %. When the content lies within this range, improvement in the rapid dissolution profile in the mouth, sufficient film strength, gummy sensation in the mouth originating in the edible polymer described below, and sticky sensation when touched by the fingers becomes possible with a particle size that is practical from a manufacturing standpoint.

Many saccharides are sweet, and this is actually a favorable property for a film-form preparation that readily dissolves in the mouth. Of course, plasticizer can also be added to the film-form preparation as desired.

The above edible polymer that is soluble both in water and a polar organic solvent is the material that forms the base of the film-form preparation of the present invention, and such an edible polymer is not particularly limited herein provided it is capable of forming a film-form preparation, is edible, it dissolves in a polar organic solvent, and the above sugar or sugar alcohol particles do not dissolve therein.

In the present description, the term "edible" refers to a pharmaceutically acceptable polymer that can be administered orally.

A preferred polar organic solvent is one wherein the above edible polymer will dissolve, but the above sugar or sugar alcohol particles will not dissolve, and an organic solvent with a solubility parameter of 9.7, for example, or higher can be suitably used. Examples of organic solvents satisfying such a solubility parameter include methanol, ethanol, isopropanol, propylene glycol, methylene chloride, and acetone. Among these, ethanol, isopropanol, methylene chloride, and acetone are preferred. If the solubility parameter of the organic solvent is less than 9.7, the sugar or sugar alcohol particles will dissolve, and dispersion as particles can become difficult.

In the present description, the term "solubility parameter" (SP value) refers to the square root of the heat of evaporation $(cal/cm^3)$ required for one mole by volume of the liquid to evaporate.

To be more specific, polyvinyl pyrrolidone (hereinafter, "PVP") and hydroxypropylcellulose (hereinafter, "HPC") can be suitably used for the above edible polymer. Both PVP and HPC are sufficiently soluble in both water and a polar organic solvent, so they satisfy both conditions of rapidly dissolving in the mouth and enabling the use of a polar organic solvent during the manufacturing process. This enables sugar or sugar alcohol particles that are insoluble in a polar organic solvent to be uniformly dispersed and carried as particles in the base of the film-form preparation.

The use of HPC as the above edible polymer is even more preferred. The hygroscopicity of HPC in relation to relative humidity is lower than that of PVP, and this is considered preferable from a practical standpoint. These materials can be used alone, or as a combination of two or more types thereof.

The time of dissolution in the mouth can be controlled by controlling the thickness of the film-form preparation of the present invention, and the time of dissolution in the mouth can be easily and intentionally controlled by suitably adjusting the molecular weight of the PVP, HPC, or other edible polymer.

The molecular weight of the PVP is preferably 2,500 to 3,000,000, and more preferably 2,500 to 1,200,000. If the molecular weight is less than 2,500, the polymer may have poor stability and hygroscopicity, and conversely, if the molecular weight exceeds 3,000,000, it may have poor solubility.

The preferred molecular weight of the PVP is 40,000 to 1,200,000 to ensure a dissolution time for the film-form preparation that is suitable for desensitization therapy using an allergen.

The molecular weight of the above HPC is preferably 10,000 to 1,150,000, and more preferably 10,000 to 370,000. If the molecular weight is less than 10,000, the polymer may have poor hygroscopicity and stability, and if the molecular weight exceeds 1,150,000, it may have poor solubility.

The preferred molecular weight of HPC is 30,000 to 370,000 to ensure a dissolution time for the film-form preparation that is suitable for desensitization therapy using an allergen.

In the present description the term molecular weight refers to the weight-average molecular weight, which can be determined by gel permeation chromatography.

The amount of hydroxypropoxy group substitution in the above HPC is preferably 50.0% or higher. In this case, the method of measuring the amount of hydroxypropoxy group substitution follows the quantitative method described in the section entitled "Hydroxypropyl cellulose" in the Official Monographs of the Fifteenth Edition of the Japanese Pharmacopoeia. A more preferred amount of hydroxypropoxy group substitution is 53.4% or higher. If the amount of substitution is less than 50.0%, the solubility of the HPC in water and the organic solvent may become poor.

The content of the above edible polymer in the film-form preparation of the present invention is preferably 1 to 80 wt % in relation to the total molecular weight of the film-form preparation. If the polymer content is less than 1 wt %, the film-form preparation of the present invention will become brittle and not exhibit sufficient strength, and if the polymer content exceeds 80 wt %, a gummy sensation originating in the edible polymer tends to occur in the mouth. A more preferred lower limit of the content of the above edible polymer is 10 wt %, and a more preferred upper limit is 70 wt %.

In addition to the edible polymer that is soluble both in water and a polar organic solvent, a suitable amount of an edible polymer that is soluble only in water, or an edible polymer that is insoluble in both water and organic polymer (hereinafter, both such edible polymers are covered by the blanket expression "other edible polymer") can be used in combination therewith provided the content is within a range that does not hinder the effect of the present invention.

Examples of the other edible polymer include synthetic polymers such as polyvinyl alcohol, carboxyvinyl polymer, hydroxypropyl methylcellulose, hydroxyethyl cellulose, methylcellulose, ethylcellulose, low-substituted hydroxypropyl cellulose, crystalline cellulose, carboxymethylcellulose sodium, carboxymethylcellulose calcium, carboxymethylcellulose, and carboxymethyl starch sodium; and polymers obtained from natural substances such as sodium alginate, dextran, casein, pullulan, pectin, guar gum, xanthan gum, tragacanth gum, acacia gum, gum arabic, gellan gum, and starch.

To define solubility in water or the polar organic solvent in the present description, if the volume of water or polar organic solvent necessary to dissolve 1 g of solute at 20° C. is 100 mL or more, the expression "insoluble" is used with respect to that solvent, and if the volume of water or polar organic solvent necessary to dissolve 1 g of solute is less than 5 mL, the expression "soluble" is used. In addition, the expression "very soluble" is used if the volume of water or polar organic solvent necessary to dissolve 1 g of solute is less than 3 mL. The solubility of the sugar or sugar alcohol particles used in the present invention is known to decrease as the temperature of the polar organic solvent increases, and by utilizing this knowledge it is possible to lower the solubility of the sugar or sugar alcohol particles even further to stabilize the same in the state of fine particles.

In addition to the above materials, the film-form preparation of the present invention can also contain a suitable amount of fragrance, flavoring, sweetener, coloring, preservative, antioxidant, stabilizer, surfactant, plasticizer (polyethylene glycol (PEG), etc.) as ingredients constituting the base of the film-form preparation.

The above allergen refers to an antigen with which an antibody of a person with an allergic disease specifically reacts.

Specific examples include allergens originating in the pollen of trees (golden acacia, red alder, white ash, American beech, birch, box elder, mountain cedar, red cedar, common cottonwood, cypress, American elm, Chinese elm, Japanese Douglas fir, sweet gum, eucalyptus, hackberry, hickory, linden, sugar maple, mesquite, mulberry, oak, olive, pecan tree, pepper tree, pine, common privet, Russian olive, American sycamore, tree of heaven, black walnut, black willow, etc.); allergens originating in the pollen of grasses (cotton, Bermuda grass, Kentucky bluegrass, smooth brome, cultivated corn, meadow fescue, Johnson grass, cultivated oats, orchard grass, redtop, perennial rye grass, rice, sweet vernal grass, timothy, careless weed, pigweed, common cocklebur, sorrel dock, goldenrod, kochia, lamb's quarters, marigold, nettle, pigwood, English plantain, giant ragweed, short ragweed, western ragweed, Russian thistle, sagebrush, Scotch broom, sheep sorrel, etc.); allergens originating in insects (silkworm, mite, honeybee, wasp, ant, cockroach, etc.); allergens originating in fungi (*Alternaria tenuis, Aspergillus fumigatus, Botrytis cinerea, Candida albicans, Cephalosporium acremonium, Curvularia spicifera, Epicoccum nigrum, Epidermophyton floccosum, Fusarium vasinfectum, Helminthosporium interseminatum, Hormodendrum cladosporioides, Mucor rasemosus, Penicillium notatum, Phoma herbarium, Pullularia pullulans, Rhizopus nigricans*, etc.); allergens originating in the skin and hair of animals (dog, cat, bird, etc.); allergens originating in house dust; and allergens originating from foods; etc. The allergen is not particularly limited herein provided it is an antigen with which an antibody of an individual with an allergic disease specifically reacts.

The content of the above allergen will differ depending on the properties, etc., thereof, but normally is $1 \times 10^{-10}$ to 60 wt % of the total weight of the film-form preparation of the present invention. If the content is less than $1 \times 10^{-10}$ wt %, the film-form preparation will not be suitable for desensitization therapy, and if the content exceeds 60 wt %, the strength of the film may markedly decrease causing a problem with the shape retention thereof.

The film-form preparation of the present invention can be manufactured by the following method, for example.

Specifically, first the above sugar or sugar alcohol particles wherein the particle size has been adjusted beforehand by pulverization, granulation, a classification device, etc., are dispersed in a suitable amount uniformly throughout the desired volume of polar organic solvent. Next, the desired amount of the above edible polymer is dissolved therein, and then the allergen is dissolved or dispersed in this solution to prepare a particle dispersion. The film-form preparation of the present invention can be manufactured by spreading a suitable amount of the resulting particle dispersion onto a publicly known release film to form a thin film thereon and then drying the same. The resulting thin film is then preferably cut to a desired shape and size, and sealed and packaged as needed to make the finished product.

The method for producing the film-form preparation in this manner is also part of the present invention.

When preparing the above particle dispersion, if bubbles should form therein, the liquid can be let stand overnight or degassed under reduced pressure.

A polar organic solvent wherein the edible polymer is soluble, but the above sugar or sugar alcohol particles are insoluble can be used when preparing the above particle dispersion. A single solvent can be used alone or a mixed solvent can be used. Specific examples include methanol, ethanol, isopropanol, propylene glycol, methylene chloride, and acetone. Among the above, ethanol, isopropanol, methylene chloride, and acetone are preferred, and purified water can be added thereto in an amount such that the sugar and sugar alcohol fine particles do not dissolve.

Effects of the Invention

The film-form preparation of the present invention enables self-administration of an allergen by the patient without the pain accompanying an injection, and the dose can be adjusted by dividing up the film-form preparation. Moreover, the film-form preparation has excellent portability, gives no sensation of a residue, and provides excellent protection against accidental swallowing because the dosage form can easily be distinguished from a tablet. The film-form preparation is also easy for a caregiver to administer, etc., and it can greatly improve the QOL of both patients and caregivers.

Additionally the film-form preparation of the present invention enables arbitrary control of the dissolution time in the mouth, especially sublingually, because it contains an edible polymer that is soluble in both water and a polar organic solvent. In a preferred embodiment, the dissolution time can be adjusted between 2 and 300 sec, so the film-form preparation of the present invention is particularly suitable for patient desensitization therapy using an allergen.

Moreover, the sugar or sugar alcohol particles do not dissolve in the polar organic solvent. Because a polar organic solvent is used to manufacture the film-form preparation of the present invention, the sugar or sugar alcohol particles can be uniformly dispersed and carried in the base of the film-form preparation in a particulate state without dissolving during the manufacturing process.

The film-form preparation of the present invention contains particles of a monosaccharide to hexasaccharide sugar or sugar alcohol thereof with an average particle size of 0.1 to 100 μm. This not only enables the film-form preparation to have sufficient film strength, but also makes it possible to reduce the gummy sensation in the mouth originating in the edible polymer and improve the feel when touched by the fingers, and obtain a high film strength.

In addition, in the method for manufacturing the film-form preparation of the present invention, it is possible to dry the same at a lower temperature by using a polar organic solvent as the solvent, and even when using allergens that cannot withstand high temperatures, the film-form preparation can be manufactured while reducing the deleterious effects thereon.

MODES FOR CARRYING OUT THE INVENTION

The present invention is described in greater detail below through examples, but is by no means limited thereto.

The particle size of the sugar or sugar alcohol particles used in the examples was adjusted by sizing using spray-drying granulation, a jet mill, pulverization and sieves. The Mass-median-diameter (D50) was measured using a laser-scattering particle size distribution analyzer, and used as an indicator of the particle sizes of the fine particles. Table 1 shows the Mass-median-diameter (D50) of the sugars and sugar alcohols that were used.

TABLE 1

| Sugar or sugar alcohol | Mass-median-diameter (D50) [um] |
|---|---|
| Mannitol fine particles | 15 |
| Mannitol fine particles A | 2 |
| Mannitol fine particles B | 33 |
| Mannitol fine particles C | 55 |
| Mannitol fine particles D | 127 |
| Lactose fine particles | 8 |
| Trehalose fine particles | 9 |
| Maltose fine particles | 13 |
| Xylitol fine particles | 21 |
| Glucose fine particles | 11 |
| Isomalt fine particles | 12 |
| Erythritol fine particles | 15 |
| Raffinose fine particles | 12 |
| Oligoglucosamine fine particles | 17 |
| D-sorbitol fine particles | 4 |
| Sucrose fine particles | 6 |

EXAMPLE 1

First 67.5 parts by weight of D-mannitol fine particles with the particle size adjusted beforehand, and 0.8 parts by weight of polyethylene glycol were added to 150.0 parts by weight of ethanol and ultrasonically dispersed. Next 64.5 parts by weight of HPC (HPC-SSL, produced by Nippon Soda Co., Ltd.) with a weight-average molecular weight of approximately 30,000 and a hydroxypropoxy substitution rate of 53.4 to 77.5% was added thereto and dissolved by stirring. Then 30.0 parts by weight of standard allergen therapy extract "Torii" cedar pollen 2000 JAU/mL (produced by Torii Pharmaceutical Co., Ltd.) was added and mixed by stirring with a rolling mixer to prepare a particle dispersion.

After the particle dispersion was thoroughly degassed, it was spread and dried on a polyester release film to produce a film with a thickness of approximately 100 μm. The resulting film was cut into 4 cm$^2$ rectangular pieces to obtain a film-form preparation.

EXAMPLE 2

A film-form preparation was prepared with the same procedure as Example 1 except acetone was used in place of ethanol.

EXAMPLE 3

A film-form preparation was prepared with the same procedure as Example 1 except the ingredients shown in Table 2 were used.

In Table 2, the term "PVP K-30" refers to polyvinylpyrrolidone (produced by Nippon Shokubai Co., Ltd.) with a weight-average molecular weight of approximately 40,000.

EXAMPLE 4

A film-form preparation was prepared with the same procedure as Example 3 except acetone was used in place of ethanol.

COMPARATIVE EXAMPLE 1

First 67.5 parts by weight of D-mannitol fine particles with the particle size adjusted beforehand, and 0.8 parts by weight of polyethylene glycol were added to 250.0 parts by weight of distilled water and ultrasonically dispersed. Next 64.5 parts by weight of pullulan (produced by Hayashibara Shoji, Inc.) was added and dissolved by stirring. Then 30.0 parts by weight of standard allergen therapy extract "Torii" cedar pollen 2000 JAU/mL (produced by Torii Pharmaceutical Co., Ltd.) was added and mixed by stirring with a rolling mixer to prepare a particle dispersion.

After the particle dispersion was thoroughly degassed, it was spread and dried on a polyester release film to produce a film with a thickness of approximately 100 μm. The resulting film was cut into 4 cm$^2$ rectangular pieces to obtain a film-form preparation.

COMPARATIVE EXAMPLE 2

A film-form preparation was prepared with the same procedure as Comparative Example 1 except the ingredients shown in Table 2 were used.

In Table 2 "HPMC" refers to hydroxypropyl methylcellulose with a weight-average molecular weight of approximately 16,000 (TC-5E, produced by Shin-Etsu Chemical Co., Ltd.)

TABLE 2

| Ingredient | Examples (parts by weight) 1 | 2 | 3 | 4 | Comparative Examples (parts by weight) 1 | 2 |
|---|---|---|---|---|---|---|
| Standard allergen therapy extract cedar pollen 2000 JAU/mL | 30.0 | 30.0 | 30.0 | 30.0 | 30.0 | 30.0 |
| HPC-SSL | 64.5 | 64.5 | — | — | — | — |
| PVP K-30 | — | — | 64.5 | 64.5 | — | — |
| Pullulan | — | — | — | — | 64.5 | — |
| HPMC | — | — | — | — | — | 64.5 |
| PEG400 | 0.8 | 0.8 | 0.8 | 0.8 | 0.8 | 0.8 |
| D-mannitol fine particles | 67.5 | 67.5 | 67.5 | 67.5 | 67.5 | 67.5 |
| Purified water | — | — | — | — | 250.0 | 240.0 |
| Ethanol | 150.0 | — | 150.0 | — | — | — |
| Acetone | — | 150.0 | — | 150.0 | — | — |

EXAMPLES 5 to 15

A film-form preparation was prepared with the same procedure as Example 1 except the ingredients shown in Table 3 were used.

TABLE 3

| Ingredient | Examples (parts by weight) 5 | 6 | 7 | 8 | 9 | 10 | 11 | 12 | 13 | 14 | 15 |
|---|---|---|---|---|---|---|---|---|---|---|---|
| Standard allergen therapy extract cedar pollen 2000 JAU/mL | 30.0 | 30.0 | 30.0 | 30.0 | 30.0 | 30.0 | 30.0 | 30.0 | 30.0 | 30.0 | 30.0 |
| HPC-SSL | 64.5 | 64.5 | 64.5 | 64.5 | 64.5 | 64.5 | 64.5 | 64.5 | 64.5 | 64.5 | 64.5 |
| PEG400 | 0.8 | 0.8 | 0.8 | 0.8 | 0.8 | 0.8 | 0.8 | 0.8 | 0.8 | 0.8 | 0.8 |
| Lactose fine particles | 67.5 | — | — | — | — | — | — | — | — | — | — |
| Trehalose fine particles | — | 67.5 | — | — | — | — | — | — | — | — | — |
| Maltose fine particles | — | — | 67.5 | — | — | — | — | — | — | — | — |
| Isomalt fine particles | — | — | — | 67.5 | — | — | — | — | — | — | — |
| Xylitol fine particles | — | — | — | — | 67.5 | — | — | — | — | — | — |
| Erythritol fine particles | — | — | — | — | — | 67.5 | — | — | — | — | — |
| Glucose fine particles | — | — | — | — | — | — | 67.5 | — | — | — | — |
| Raffinose fine particles | — | — | — | — | — | — | — | 67.5 | — | — | — |
| Oligoglucosamine fine particles | — | — | — | — | — | — | — | — | 67.5 | — | — |
| D-sorbitol fine particles | — | — | — | — | — | — | — | — | — | 67.5 | — |
| Sucrose fine particles | — | — | — | — | — | — | — | — | — | — | 67.5 |
| Ethanol | 150.0 | 150.0 | 150.0 | 150.0 | 150.0 | 150.0 | 140.0 | 170.0 | 140.0 | 150.0 | 150.0 |

COMPARATIVE EXAMPLE 3

First 0.8 parts by weight of polyethylene glycol was added to 220.0 parts by weight of ethanol and dispersed ultrasonically. Next 132.0 parts by weight of HPC (HPC-SSL, produced by Nippon Soda Co., Ltd.) with a weight-average molecular weight of approximately 30,000 and a hydroxypropoxy substitution rate of 53.4 to 77.5% was added thereto and dissolved by stirring. Then 30.0 parts by weight of standard allergen therapy extract "Torii" cedar pollen 2000 JAU/mL (produced by Torii Pharmaceutical Co., Ltd.) was added and mixed by stirring with a rolling mixer to prepare a particle dispersion.

After the particle dispersion was thoroughly degassed, it was spread and dried on a polyester release film to produce a film with a thickness of approximately 100 μm. The resulting film was cut into 4 cm² rectangular pieces to obtain a film-form preparation.

COMPARATIVE EXAMPLE 4

First 67.5 parts by weight of D-mannitol fine particles with the particle size adjusted beforehand, and 0.8 parts by weight of polyethylene glycol were added to 200.0 parts by weight of distilled water and ultrasonically dispersed. Next 64.5 parts by weight of HPC (HPC-SSL, produced by Nippon Soda Co., Ltd.) with a weight-average molecular weight of approximately 30,000 and a hydroxypropoxy substitution rate of 53.4 to 77.5% was added thereto and dissolved by stirring. Then 30.0 parts by weight of standard allergen therapy extract "Torii" cedar pollen 2000 JAU/mL (produced by Torii Pharmaceutical Co., Ltd.) was added and mixed by stirring with a rolling mixer to prepare a particle dispersion.

After the particle dispersion was thoroughly degassed, it was spread and dried on a polyester release film. When the attempt was made to release the film from the polyester release film to obtain a film-form preparation, the film was actually too soft and brittle so a film-form preparation could not be obtained.

COMPARATIVE EXAMPLES 5 to 15

Attempts were made to prepare a film-form preparation with the same procedure as Comparative Example 4 using the ingredients shown in Table 4, but just as in the case of Comparative Example 4, film-form preparations could not be obtained except in the case of Comparative Examples 5, 6, 8, and 13. In Comparative Examples 5, 6, 8, and 13, the films were each cut into 4cm² pieces to obtain a film-form preparation.

COMPARATIVE EXAMPLE 16

First 0.8 parts by weight of polyethylene glycol was added to 250.0 parts by weight of distilled water and dispersed ultrasonically. Next 132.0 parts by weight of HPC (HPC-SSL, produced by Nippon Soda Co., Ltd.) with a weight-average molecular weight of approximately 30,000 and a hydroxypropoxy substitution rate of 53.4 to 77.5% was added thereto and dissolved by stirring. Then 30.0 parts by weight of standard allergen therapy extract "Torii" cedar pollen 2000 JAU/mL (produced by Torii Pharmaceutical Co., Ltd.) was added and mixed by stirring with a rolling mixer to prepare a particle dispersion.

After the particle dispersion was thoroughly degassed, it was spread and dried on a polyester release film to produce a film with a thickness of approximately 100 μm. The resulting film was cut into 4 cm² rectangular pieces to obtain a film-form preparation.

TABLE 4

| Ingredient | Comparative Examples (parts by weight) | | | | | | | | | | | | | |
|---|---|---|---|---|---|---|---|---|---|---|---|---|---|---|
| | 3 | 4 | 5 | 6 | 7 | 8 | 9 | 10 | 11 | 12 | 13 | 14 | 15 | 16 |
| Standard allergen therapy extract cedar pollen 2000 JAU/mL | 30.0 | 30.0 | 30.0 | 30.0 | 30.0 | 30.0 | 30.0 | 30.0 | 30.0 | 30.0 | 30.0 | 30.0 | 30.0 | 30.0 |
| HPC-SSL | 132.0 | 64.5 | 64.5 | 64.5 | 64.5 | 64.5 | 64.5 | 64.5 | 64.5 | 64.5 | 64.5 | 64.5 | 64.5 | 132.0 |
| PEG400 | 0.8 | 0.8 | 0.8 | 0.8 | 0.8 | 0.8 | 0.8 | 0.8 | 0.8 | 0.8 | 0.8 | 0.8 | 0.8 | 0.8 |
| D-mannitol fine particles | — | 67.5 | — | — | — | — | — | — | — | — | — | — | — | — |
| Lactose fine particles | — | — | 67.5 | — | — | — | — | — | — | — | — | — | — | — |
| Trehalose fine particles | — | — | — | 67.5 | — | — | — | — | — | — | — | — | — | — |
| Maltose fine particles | — | — | — | — | 67.5 | — | — | — | — | — | — | — | — | — |
| Isomalt fine particles | — | — | — | — | — | 67.5 | — | — | — | — | — | — | — | — |
| Xylitol fine particles | — | — | — | — | — | — | 67.5 | — | — | — | — | — | — | — |
| Erythritol fine particles | — | — | — | — | — | — | — | 67.5 | — | — | — | — | — | — |
| Glucose fine particles | — | — | — | — | — | — | — | — | 67.5 | — | — | — | — | — |
| Raffinose fine particles | — | — | — | — | — | — | — | — | — | 67.5 | — | — | — | — |
| Oligoglucosamine fine particles | — | — | — | — | — | — | — | — | — | — | 67.5 | — | — | — |
| D-sorbitol fine particles | — | — | — | — | — | — | — | — | — | — | — | 67.5 | — | — |
| Sucrose fine particles | — | — | — | — | — | — | — | — | — | — | — | — | 67.5 | — |
| Ethanol | 220.0 | — | — | — | — | — | — | — | — | — | — | — | — | — |
| Purified water | — | 200.0 | 200.0 | 200.0 | 200.0 | 200.0 | 200.0 | 200.0 | 200.0 | 200.0 | 200.0 | 200.0 | 200.0 | 250.0 |

EXAMPLE 16

First 67.5 parts by weight of D-mannitol fine particles with the particle size adjusted beforehand, and 0.8 parts by weight of polyethylene glycol were added to 150.0 parts by weight of ethanol and ultrasonically dispersed. Next 64.5 parts by weight of HPC (HPC-SSL, produced by Nippon Soda Co., Ltd.) with a weight-average molecular weight of approximately 30,000 and a hydroxypropoxy substitution rate of 53.4 to 77.5% was added thereto and dissolved by stirring. Then 30.0 parts by weight of therapeutic allergen extract for subcutaneous injection "Torii" Japanese red pine pollen 1:100 (produced by Torii Pharmaceutical Co., Ltd.) was added and mixed by stirring with a rolling mixer to prepare a particle dispersion.

After the particle dispersion was thoroughly degassed, it was spread and dried on a polyester release film to produce a film with a thickness of approximately 100 μm. The resulting film was cut into 4 cm² rectangular pieces to obtain a film-form preparation.

EXAMPLES 17 to 27

Films were prepared with same procedure as Example 16 using the ingredients shown in Table 5 to obtain film-form preparations. The following allergens were used: therapeutic allergen extract for subcutaneous injection "Torii" spinach pollen 1:100 (produced by Torii Pharmaceutical Co., Ltd.), therapeutic allergen extract for subcutaneous injection "Torii" ragweed pollen 1:100 (produced by Torii Pharmaceutical Co., Ltd.), therapeutic allergen extract for subcutaneous injection "Torii" buckwheat powder 1:10 (produced by Torii Pharmaceutical Co., Ltd.), therapeutic allergen extract for subcutaneous injection "Torii" silk 1:10 (produced by Torii Pharmaceutical Co., Ltd.), therapeutic allergen extract for subcutaneous injection "Torii" cotton 1:10 (produced by Torii Pharmaceutical Co., Ltd.), therapeutic allergen extract for subcutaneous injection "Torii" house dust 1:10 (produced by Torii Pharmaceutical Co., Ltd.), therapeutic allergen extract for subcutaneous injection "Torii" *Aspergillus* 1:1000 (produced by Torii Pharmaceutical Co., Ltd.), therapeutic allergen extract for subcutaneous injection "Torii" *Alternaria* 1:1000 (produced by Torii Pharmaceutical Co., Ltd.), therapeutic allergen extract for subcutaneous injection "Torii" *Candida* 1:1000 (produced by Torii Pharmaceutical Co., Ltd.), therapeutic allergen extract for subcutaneous injection "Torii" *Cladosporium* 1:1000 (produced by Torii Pharmaceutical Co., Ltd.), and therapeutic allergen extract for subcutaneous injection "Torii" Penicillium 1:1000 (produced by Torii Pharmaceutical Co., Ltd.).

TABLE 5

| Ingredient | Examples [parts by weight] | | | | | | | | | | | |
|---|---|---|---|---|---|---|---|---|---|---|---|---|
| | 16 | 17 | 18 | 19 | 20 | 21 | 22 | 23 | 24 | 25 | 26 | 27 |
| Therapeutic allergen extract for subcutaneous injection Japanese red pine pollen 1:100 | 30.0 | — | — | — | — | — | — | — | — | — | — | — |
| Therapeutic allergen extract for subcutaneous injection spinach pollen 1:100 | — | 30.0 | — | — | — | — | — | — | — | — | — | — |
| Therapeutic allergen extract for subcutaneous injection ragweed pollen 1:100 | — | — | 30.0 | — | — | — | — | — | — | — | — | — |
| Therapeutic allergen extract for subcutaneous injection buckwheat powder 1:10 | — | — | — | 30.0 | — | — | — | — | — | — | — | — |
| Therapeutic allergen extract for subcutaneous injection silk 1:10 | — | — | — | — | 30.0 | — | — | — | — | — | — | — |
| Therapeutic allergen extract for subcutaneous injection cotton 1:10 | — | — | — | — | — | 30.0 | — | — | — | — | — | — |
| Therapeutic allergen extract for subcutaneous injection house dust 1:10 | — | — | — | — | — | — | 30.0 | — | — | — | — | — |
| Therapeutic allergen extract for subcutaneous injection *Aspergillus* 1:1000 | — | — | — | — | — | — | — | 30.0 | — | — | — | — |
| Therapeutic allergen extract for subcutaneous injection *Alternaria* 1:1000 | — | — | — | — | — | — | — | — | 30.0 | — | — | — |

TABLE 5-continued

| Ingredient | Examples [parts by weight] | | | | | | | | | | | |
|---|---|---|---|---|---|---|---|---|---|---|---|---|
| | 16 | 17 | 18 | 19 | 20 | 21 | 22 | 23 | 24 | 25 | 26 | 27 |
| Therapeutic allergen extract for subcutaneous injection *Candida* 1:1000 | — | — | — | — | — | — | — | — | — | 30.0 | — | — |
| Therapeutic allergen extract for subcutaneous injection *Cladosporium* 1:1000 | — | — | — | — | — | — | — | — | — | — | 30.0 | — |
| Therapeutic allergen extract for subcutaneous injection *Penicillium* 1:1000 | — | — | — | — | — | — | — | — | — | — | — | 30.0 |
| HPC-SSL | 64.5 | 64.5 | 64.5 | 64.5 | 64.5 | 64.5 | 64.5 | 64.5 | 64.5 | 64.5 | 64.5 | 64.5 |
| PEG400 | 0.8 | 0.8 | 0.8 | 0.8 | 0.8 | 0.8 | 0.8 | 0.8 | 0.8 | 0.8 | 0.8 | 0.8 |
| D-mannitol fine particles | 67.5 | 67.5 | 67.5 | 67.5 | 67.5 | 67.5 | 67.5 | 67.5 | 67.5 | 67.5 | 67.5 | 67.5 |
| Ethanol | 150.0 | 150.0 | 150.0 | 150.0 | 150.0 | 150.0 | 150.0 | 150.0 | 150.0 | 150.0 | 150.0 | 150.0 |

EXAMPLE 28

First 68.5 parts by weight of D-mannitol fine particles with the particle size adjusted beforehand, and 4.0 parts by weight of polyethylene glycol were added to 130.0 parts by weight of ethanol and ultrasonically dispersed. Next 10.0 parts by weight of Japanese cedar pollen (produced by Asahi Food & Healthcare Co., Ltd.) and 65.3 parts by weight of HPC (HPC-SSL, produced by Nippon Soda Co., Ltd.) with a weight-average molecular weight of approximately 30,000 and a hydroxypropoxy substitution rate of 53.4 to 77.5% were added thereto and dissolved by stirring to prepare a particle dispersion.

After the particle dispersion was thoroughly degassed, it was spread and dried on a polyester release film to produce a film with a thickness of approximately 100 μm. The resulting film was cut into 4 cm² rectangular pieces to obtain a film-form preparation.

EXAMPLES 29 to 31

Films were prepared with the same procedure as Example 28 using Purified Cedar Pollen Antigen Cryj1 (produced by Hayashibara Biochemical Laboratories, Inc.) and Purified Cedar Pollen Antigen Cryj2 (produced by Hayashibara Biochemical Laboratories, Inc.), and the ingredients shown in Table 6 to obtain film-form preparations.

TABLE 6

| Ingredient | Examples [parts by weight] | | | |
|---|---|---|---|---|
| | 28 | 29 | 30 | 31 |
| Japanese cedar pollen | 10.0 | — | — | — |
| Purified cedar pollen antigen Cryj1 | — | 0.5 | — | 0.5 |
| Purified cedar pollen antigen Cryj2 | — | — | 0.5 | 0.5 |
| HPC-SSL | 65.3 | 69.8 | 69.8 | 69.6 |
| PEG400 | 4.0 | 4.0 | 4.0 | 4.0 |
| D-mannitol fine particles | 68.5 | 74.0 | 74.0 | 73.7 |
| Ethanol | 130.0 | 130.0 | 130.0 | 130.0 |

EXAMPLE 32

First 50.0 parts by weight of D-mannitol fine particles A with the particle size adjusted beforehand, and 1.0 parts by weight of polyethylene glycol were added to 100.0 parts by weight of ethanol and ultrasonically dispersed. Next 44.0 parts by weight of HPC (HPC-SSL, produced by Nippon Soda Co., Ltd.) with a weight-average molecular weight of approximately 30,000 and a hydroxypropoxy substitution rate of 53.4 to 77.5% was added thereto and dissolved by stirring. Then 10.0 parts by weight of standard allergen therapy extract "Torii" cedar pollen 2000 JAU/mL (produced by Torii Pharmaceutical Co., Ltd.) was added and mixed by stirring with a rolling mixer to prepare a particle dispersion.

After the particle dispersion was thoroughly degassed, it was spread and dried on a polyester release film to produce a film with a thickness of approximately 100 μm. The resulting film was cut into 4 cm² rectangular pieces to obtain a film-form preparation.

EXAMPLES 33 to 35

Films were prepared with the same procedure as Example 32 using D-mannitol fine particles B and D-mannitol fine particles C with the particle size adjusted beforehand, and the ingredients shown in Table 7 to obtain film-form preparations.

EXAMPLES 36 to 39, COMPARATIVE EXAMPLE 17

Films were prepared with the same procedure as Example 32 using HPC (HPC-SSL, produced by Nippon Soda Co., Ltd.) with a weight-average molecular weight of approximately 30,000 and a hydroxypropoxy substitution rate of 53.4 to 77.5% and HPC (HPC-L, produced by Nippon Soda Co., Ltd.) with a weight-average molecular weight of approximately 140,000 and an amount of hydroxypropyl group substitution rate of 53.4 to 77.5%, and the ingredients shown in Table 7 to obtain film-form preparations.

In this case, films were prepared with the following thicknesses: Example 35, 250 μm; Example 36, 120 μm, Example 37, 120 μm; Example 38, 120 μm; and Example 39, 80 μm.

TABLE 7

| Ingredient | Example (parts by weight) | | | | | | | | Comparative Example (parts by weight) |
|---|---|---|---|---|---|---|---|---|---|
| | 32 | 33 | 34 | 35 | 36 | 37 | 38 | 39 | 17 |
| standard allergen therapy extract cedar pollen 2000 JAU/mL | 10.0 | 10.0 | 10.0 | 10.0 | 10.0 | 10.0 | 10.0 | 10.0 | 10.0 |

TABLE 7-continued

| Ingredient | Example (parts by weight) | | | | | | | | Comparative Example (parts by weight) |
|---|---|---|---|---|---|---|---|---|---|
| | 32 | 33 | 34 | 35 | 36 | 37 | 38 | 39 | 17 |
| HPC-SSL | 44.0 | 44.0 | 44.0 | — | — | 74.0 | 4.0 | 4.0 | 44.0 |
| HPC-L | — | — | — | 91.0 | 91.0 | — | 15.0 | 15.0 | — |
| PEG400 | 1.0 | 1.0 | 1.0 | 1.0 | 1.0 | 1.0 | 1.0 | 1.0 | 1.0 |
| D-mannitol fine particles A | 50.0 | — | — | 2.0 | 2.0 | 25.0 | 75.0 | 75.0 | — |
| D-mannitol fine particles B | — | 50.0 | — | — | — | — | — | — | — |
| D-mannitol fine particles C | — | — | 50.0 | — | — | — | — | — | — |
| D-mannitol fine particles D | — | — | — | — | — | — | — | — | 50.0 |
| Ethanol | 100.0 | 100.0 | 100.0 | 270.0 | 270.0 | 140.0 | 80.0 | 80.0 | 100.0 |

[Test Methods]

Measurements and evaluations were carried out on the film-form preparations prepared in these examples and comparative examples for dissolution profile in the mouth, film strength, gummy sensation in the mouth, and feel when touched by the fingers by peeling test, oral dissolution test, stiffness test, tensile strength test, tack duration test, and sensory test (feel), respectively. The particle size of the sugar or sugar alcohol particles dispersed in the film-form preparation was measured by microscopic examination. Each test method is described below.

(1) Oral Dissolution Test

First 900 mL of pH 6.8 phosphate buffer was placed in a 1000 mL low glass petri dish, a stainless steel mesh basket (φ 4 mm) was inverted and submerged therein, and agitation was provided by a stirrer (300 rpm). The temperature of the liquid was maintained at 37±2° C. using a constant temperature water circulator. A test piece (4 cm$^2$) was submerged, and concurrently a 3 cm$^2$×3 cm$^2$ stainless steel screen (5 mm mesh) was placed on top as a sinker. The duration from the time the test piece was submerged until the test piece had finished disintegrating was checked visually and measured with a stop watch. The measurement of each sample was repeated 3 times, and the mean was used as the oral dissolution time. The oral dissolution time was then given a score using the following criteria.
4: 0 to 10 sec
3: 10 to 15 sec
2: 15 to 20 sec
1: 20 sec or longer Prepared film-form preparations that could not be physically released from the release film were given a score of 0. For Examples 35 to 39 that were prepared for the purpose of controlling the dissolution time, the actual dissolution time was recorded.

(2) Tensile Strength Test

A small, tabletop, vertical tensile test apparatus (produced by Shimadzu Corporation, EZ TEST-100M) was used following "JIS K7127 Testing Method for Tensile Properties of Plastic Films and Sheets." The film-form preparation was cut to a 12 mm×50 mm test sample, and the test was performed after thorough drying in a desiccator. A rate of 60 mm/min was used as the draw rate. Because almost no stretching was seen in the test samples, the tensile strength at the measured yield point was used as the tensile strength.

The test was repeated 3 times for each sample, and the mean value was recorded as the tensile strength. The tensile strength was then given a score using the following criteria.
4: 10 to 20 N
3: 5 to 10 N
2: 2 to 5 N
1: 0 to 2 N Prepared film-form preparations that could not be physically released from the release film were given a score of 0.

(3) Stiffness Test

This test was performed following the test method of "JIS L1096 Testing Methods for Woven Fabrics, 8.19 Stiffness, 8.19.1 Method A (45° cantilever method). In this test five 20 mm×150 mm test pieces were selected, and the short dimension of the test piece was aligned with the baseline of the scale on a smooth-surfaced, flat platform with one end having a 45° downward slope. Next, the test piece was gently slid in the direction of the slope by a suitable method, and when the center point of an edge of the test piece came into contact with the slope A, the position of the trailing edge was read on the scale. Stiffness is expressed as the length (mm) that the test piece was moved. Stiffness was determined by measuring the five test pieces both top up and bottom up, and both forward and backward, and then calculating the mean value. The criteria were established as follows using a stiffness of approximately 50 mm for a film-form preparation to which no sugar was added (Comparative Example 3) as a standard.
4: 50±10 mm
3: 50±20 mm
2: 50±30 mm
1: 50±40 mm or more Prepared film-form preparations that could not be physically released from the release film were given a score of 0.

(4) Tack Duration Test

Figure 2:
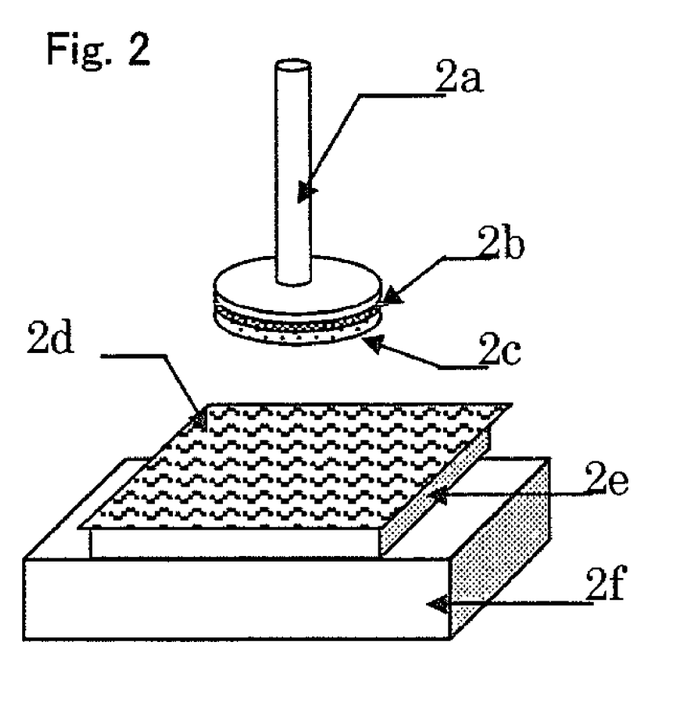
FIG. 2 is a schematic drawing of the tack duration test.

The test was performed under the environment shown in FIG. 2 using a rheometer (SUN SCIENTIFIC, CR-2000). First, a 12 mm diameter test piece 2c was adhered to a 12 mm diameter probe 2a with double-sided tape 2b. Separately, a piece of rubber 2e was mounted on the test platform 2f, and a collagen film 2d soaked with water was placed thereon. Then 200 μL of purified water was applied to the test piece, the probe 2a with the test piece 2c adhered thereto was lowered, placed in contact with the top of the collagen film 2d, and then raised. At that time, the tack duration after the initial tack, which was obtained when the probe 2a released from the collagen film 2d, was measured using slide caliper from recording paper. The criteria were as follows.
4: 0 to 2 mm
3: 2 to 3 mm
2: 3 to 4 mm
1: 4 mm or more In the case of the comparative examples in which the prepared film-form preparation could not release from the polyethylene terephthalate release film, each release film was cut, the release film side was adhered to the probe with double-sided tape, and tack duration was measured in the same manner.

(5) Sensory Test (Feel)

Film-form preparations cut from the examples and comparative examples were evaluated for the unpleasant sensation of a sticky sensation on the surface by actually tracing a circle thereon with the fingers for 5 sec. The criteria were as follows.
4: No a sticky sensation
3: Slightly sticky but not unpleasant
2: Unpleasant sticky sensation
1: Very sticky, and film remains on the fingers.

Prepared film-form preparations that could not be physically released from the release film were given a score of 0.

(6) Peeling Test

The peeling properties from the polyethylene terephthalate release film were evaluated at the time the films were prepared. The criteria were as follows.
4: Can be peeled off easily
3: Can be peeled off
2: Can be peeled off with some effort
1: Can be peeled off with effort, but film tears
0: Cannot be peeled off at all The results of the oral dissolution test, tensile strength test, stiffness test, tack duration test, and sensory test (feel) are shown as follows: Examples 1 to 15—Table 8, Comparative Examples 1 to 16—Table 9, Examples 16 to 27—Table 10, Examples 28 to 31—Table 11, Examples 32 to 34 and Comparative Example 17—Table 12. Table 13 shows the results of the dissolution tests for Examples 35 to 39.

A relative evaluation of the examples was performed by totaling the scores of the six test parameters and comparing the total scores.

(7) Measurement of Particle Size in Film-form Preparations by Microscopic Examination In Examples 32 to 34 the particle size of the added D-mannitol fine particles A to C in the films were actually measured using a microscope (produced by Keyence Corporation, THX-600). Two hundred particles were measured and the Mass-median-diameter (D50) was determined.

Table 14 shows the results of the Mass-median-diameter (D50) of the D-mannitol fine particles in the film-form preparations of Examples 32 to 34 and Comparative Example 17. For comparison reason, the particle size prior to the addition is also shown.

TABLE 8

| Example | Peeling | Stiffness | Tensile strength | Tack duration | Oral dissolution time | Sensory (feel) | Total |
|---|---|---|---|---|---|---|---|
| 1 | 4 | 4 | 4 | 4 | 4 | 4 | 24 |
| 2 | 4 | 4 | 4 | 4 | 4 | 4 | 24 |
| 3 | 4 | 3 | 3 | 4 | 4 | 3 | 21 |
| 4 | 4 | 3 | 3 | 4 | 4 | 4 | 22 |
| 5 | 4 | 4 | 4 | 4 | 3 | 4 | 23 |
| 6 | 4 | 4 | 4 | 4 | 4 | 4 | 24 |
| 7 | 4 | 4 | 4 | 4 | 4 | 2 | 22 |
| 8 | 4 | 4 | 4 | 4 | 4 | 4 | 24 |
| 9 | 4 | 3 | 3 | 4 | 4 | 4 | 22 |
| 10 | 4 | 4 | 3 | 4 | 4 | 3 | 20 |
| 11 | 4 | 4 | 4 | 4 | 4 | 3 | 18 |
| 12 | 4 | 3 | 3 | 4 | 3 | 3 | 20 |
| 13 | 4 | 3 | 3 | 4 | 4 | 3 | 21 |
| 14 | 4 | 4 | 4 | 4 | 4 | 4 | 24 |
| 15 | 4 | 4 | 3 | 4 | 4 | 4 | 23 |

As shown in Table 8, the film-form preparations of Examples 1 to 15 all had excellent scores in each evaluation parameter, and excellent scores were obtained with a variety of polar organic solvents. Although the sensory test score for the film-form preparation of Example 7 is slightly poorer, the overall score was excellent.

EXAMPLE A

The film-form preparation of Example A is manufactured using the same procedure as Example 1 except methylene chloride is used in place of ethanol. Just as in the film-form preparation of Example 1, the film-form preparation of Example A has excellent scores in the peeling test, oral dissolution test, stiffness test, tensile strength test, tack duration test, and sensory test (feel).

EXAMPLE B

The film-form preparation of Example B is manufactured using the same procedure as Example 1 except isopropanol is used in place of ethanol. Just as in the film-form preparation of Example 1, the film-form preparation of Example B has excellent scores in the peeling test, oral dissolution test, stiffness test, tensile strength test, tack duration test, and sensory test (feel).

TABLE 9

| Comparative Example | Peeling | Stiffness | Tensile strength | Tack duration | Oral dissolution time | Sensory (feel) | Total |
|---|---|---|---|---|---|---|---|
| 1 | 2 | 1 | 1 | 2 | 3 | 2 | 11 |
| 2 | 4 | 2 | 3 | 2 | 3 | 2 | 16 |
| 3 | 4 | 4 | 4 | 1 | 2 | 2 | 17 |
| 4 | 0 | 0 | 0 | 4 | 0 | 0 | 4 |
| 5 | 1 | 0 | 0 | 3 | 0 | 1 | 5 |
| 6 | 1 | 0 | 0 | 4 | 0 | 1 | 6 |
| 7 | 0 | 0 | 0 | 3 | 0 | 0 | 3 |
| 8 | 1 | 0 | 0 | 4 | 0 | 1 | 6 |
| 9 | 0 | 0 | 0 | 4 | 0 | 0 | 4 |
| 10 | 0 | 0 | 0 | 2 | 0 | 0 | 2 |
| 11 | 0 | 0 | 0 | 1 | 0 | 0 | 1 |
| 12 | 0 | 0 | 0 | 2 | 0 | 0 | 2 |
| 13 | 1 | 0 | 0 | 4 | 0 | 0 | 5 |
| 14 | 0 | 0 | 0 | 3 | 0 | 0 | 3 |
| 15 | 1 | 0 | 0 | 2 | 0 | 2 | 5 |
| 16 | 2 | 4 | 4 | 1 | 2 | 2 | 15 |

As shown in Table 9, the film-form preparation of Comparative Example 1 containing pullulan, which is an edible polymer soluble only in water, had poor peeling properties, had low scores for bend deformation and tensile strength, and felt sticky. The film-form preparation of Comparative Example 2 containing HPMC, which is an edible polymer soluble only in water, had a low score for bend deformation and felt sticky. The film-form preparation of Comparative Example 3, which did not contain sugar or sugar alcohol particles, had poor oral dissolution and felt sticky. Comparative Examples 4 to 15, which were prepared by dissolving HPC in purified water, did not yield films with sufficient strength. More specifically, the film-form preparations of Comparative Examples 4, 7, and 9 to 12 had a plurality of crystallized sugar or sugar alcohol particles produced by a one-time dissolution and recrystallization of the sugar or sugar alcohol particles. In the film-form preparations of these Comparative Examples, the average particle size of the sugar or sugar alcohol crystals fell outside the range of 0.1 to 100 μm, so the strength of the film-form preparations decreased (i.e., they became brittle). The film-form preparation of Comparative Example 16, which was prepared by dissolving HPC in purified water and did not contain sugar or sugar alcohol particles, had poor oral dissolution and felt sticky.

TABLE 10

| Example | Peeling | Stiffness | Tensile strength | Tack duration | Oral dissolution time | Sensory (feel) | Total |
|---|---|---|---|---|---|---|---|
| 16 | 4 | 4 | 4 | 4 | 4 | 4 | 24 |
| 17 | 4 | 4 | 4 | 4 | 4 | 4 | 24 |
| 18 | 4 | 4 | 4 | 3 | 4 | 4 | 23 |
| 19 | 4 | 4 | 4 | 3 | 4 | 4 | 23 |
| 20 | 4 | 4 | 4 | 4 | 4 | 4 | 24 |
| 21 | 4 | 4 | 4 | 4 | 4 | 4 | 24 |
| 22 | 4 | 2 | 4 | 4 | 3 | 4 | 21 |
| 23 | 4 | 4 | 4 | 4 | 4 | 4 | 24 |
| 24 | 4 | 4 | 4 | 3 | 4 | 4 | 23 |
| 25 | 4 | 4 | 4 | 4 | 4 | 4 | 24 |
| 26 | 4 | 4 | 4 | 3 | 4 | 4 | 23 |
| 27 | 4 | 4 | 4 | 4 | 4 | 4 | 24 |

As shown in Table 10, the film-form preparations of Examples 16 to 27 had excellent results in all of the evaluation parameters when formulated with various allergens.

TABLE 11

| Example | Peeling | Stiffness | Tensile strength | Tack duration | Oral dissolution time | Sensory (feel) | Total |
|---|---|---|---|---|---|---|---|
| 28 | 4 | 4 | 4 | 4 | 4 | 4 | 24 |
| 29 | 4 | 4 | 4 | 4 | 4 | 4 | 24 |
| 30 | 4 | 4 | 4 | 4 | 4 | 4 | 24 |
| 31 | 4 | 4 | 4 | 4 | 4 | 4 | 24 |

As shown in Table 11, the film-form preparations of Examples 28 to 31, wherein the type of cedar pollen as the allergen and the composition of various ingredients were varied in relation to Example 1, had excellent results in all of the evaluation parameters.

TABLE 12

| | | Peeling | Stiffness | Tensile strength | Tack duration | Oral dissolution time | Sensory (feel) | Total |
|---|---|---|---|---|---|---|---|---|
| Example | 32 | 4 | 4 | 4 | 4 | 4 | 4 | 24 |
| | 33 | 4 | 3 | 3 | 4 | 3 | 4 | 21 |
| | 34 | 4 | 3 | 2 | 4 | 3 | 4 | 20 |
| Comparative example | 17 | 1 | 2 | 1 | 4 | 3 | 3 | 14 |

As shown in Table 12, the film-form preparation of Example 32, which used D-mannitol fine particles A having an average particle size of 2 μm had excellent results in all of the evaluation parameters. However, the scores for bend deformation and tensile strength, and the oral dissolution results were poorer for the film-form preparations of Examples 33 and 34 than for the film-form preparation of Example 32. Those examples contained D-mannitol fine particles B (average article size 33 μm) and D-mannitol fine particles C (average particle size 55 μm), respectively, which have a greater average particle size than the D-mannitol fine particles A of Example 32.

In addition, the film-form preparation of Comparative Example 17 containing D-mannitol fine particles D with an average particle size of 127 μm had poorer results in terms of peeling properties and strength than the film-form preparations of the examples.

TABLE 13

| Example | Oral dissolution time (sec) |
|---|---|
| 35 | 176 |
| 36 | 42 |
| 37 | 28 |
| 38 | 8 |
| 39 | 4 |

As shown in Table 13, the oral dissolution time was 176 sec for the film-form preparation of Example 35, which used HPC with a molecular weight of approximately 140,000 as the soluble polymer and had a film thickness of 250 μm. The film-form preparation of Example 36, which was prepared in the same manner as Example 35 except the film thickness was 120 μm, had an oral dissolution time of 42 sec.

The oral dissolution time was 28 sec for the film-form preparation of Example 37, which used HPC with a molecular weight of approximately 30,000 as the soluble polymer and had a film thickness of 120 μm.

The oral dissolution time was 8 sec for the film-form preparation of Example 38, which used a combination of HPC with molecular weights of approximately 30,000 and approximately 140,000 as the soluble polymer and had a film thickness of 120 μm. The film-form preparation of Example 39, which was prepared in the same manner as Example 38 except the film thickness was 80 μm, had an oral dissolution time of 4 sec.

Thus, these results show that it is possible to control the oral dissolution time easily by adjusting the molecular weight of the soluble polymer and the film thickness of the film-form preparation.

TABLE 14

| | | Mass-median-diameter (D50) (um) of D-mannitol fine particles before addition | Mass-median-diameter (D50) (um) of D-mannitol fine particles in film-form preparation |
|---|---|---|---|
| Example | 32 | 2 | 3 |
| | 33 | 33 | 31 |
| | 34 | 55 | 59 |
| Comparative Example | 17 | 127 | 134 |

As shown in Table 14, the Mass-median-diameter (D50) of the D-mannitol fine particles in the film-form preparations of Examples 32 to 34 and Comparative Example 17 is practically the same as in the film-form preparation and before addition, and this shows that the D-mannitol fine particles are dispersed as particles without dissolving in the film-form preparation.

Industrial Applicability

In the film-form preparation of the present invention, sugar and sugar alcohol are dispersed in a particulate state, and as a result the following properties are clearly superior to prior art products: a controllable dissolution profile in the mouth, particularly sublingually; adequate film strength; decreased gummy sensation in the mouth due to the presence of the water-soluble polymer; and feel when touched by the fingers. Uniformly dispersing the sugar and sugar alcohol in a particulate state throughout the film enables clear improvement of only those properties necessary for taking the medication such as solubility in the mouth, feel of the film when touched, feel of the film in the mouth, etc., without the loss of film properties relevant to manufacturing such as necessary tensile strength and stiffness.

When purified water or a mixture of purified water and a polar organic solvent is used instead of an organic solvent as the solvent in preparing a film, the added sugar and sugar alcohol particles dissolve, and this greatly affects film properties. To solve this problem, the content of sugar and sugar alcohol must be reduced, but with such a method, the content ratio of edible polymer to the whole is increased, and as a result, necessary properties such as solubility in the mouth, feel of the film when touched, feel of the film in the mouth, etc., are diminished. The present invention provides a mode and composition of a film-form preparation containing allergen that adequately resolves these problems.

Explanation of Symbols

| | |
|---|---|
| 1a | One or two or more types of particles selected from the group consisting of monosaccharide to hexasaccharide sugars and sugar alcohols thereof |
| 1b | Base |
| 2a | Probe |
| 2b | Double-sided tape |
| 2c | Test piece |
| 2d | Collagen film |
| 2e | Rubber |
| 2f | Test platform |

The invention claimed is:

1. A film-form preparation comprising:
pollen;
an edible polymer that is soluble in both water and a polar organic solvent; and
one or two or more types of particles selected from the group consisting of monosaccharide to hexasaccharide sugars and sugar alcohols thereof that have an average particle size of 0.1 to 100 μm.

2. The film-form preparation according to claim 1, wherein the particles of the monosaccharide to hexasaccharide sugars or sugar alcohols thereof have an average particle size of 0.1 to 30 μm.

3. The film-form preparation according to claim 1, wherein the monosaccharide to hexasaccharide sugars are non-reducing sugars.

4. The film-form preparation according to claim 1, wherein the edible polymer that is soluble in both water and a polar organic solvent is polyvinyl pyrrolidone and/or hydroxypropylcellulose.

5. The film-form preparation according to claim 4, wherein the molecular weight of the polyvinyl pyrrolidone ranges from 2500 to 3,000,000.

6. The film-form preparation according to claim 4, wherein the molecular weight of the hydroxypropylcellulose ranges from 10,000 to 1,200,000.

7. The film-form preparation according to claim 1, wherein the pollen a pollen originating from trees or a pollen originating from grasses.

8. The film-form preparation according to claim 7, wherein the pollen originates the pollen of golden acacia, red alder, white ash, American beech, birch, box elder, mountain cedar, red cedar, common cottonwood, cypress, American elm, Chinese elm, Japanese Douglas fir, sweet gum, eucalyptus, hackberry, hickory, linden, sugar maple, mesquite, mulberry, oak, olive, pecan tree, pepper tree, pine, common privet, Russian olive, American sycamore, tree of heaven, black walnut, or black willow.

9. The film-form preparation according to claim 7, wherein the pollen originates in the pollen of cotton, Bermuda grass, Kentucky bluegrass, smooth brome, cultivated corn, meadow fescue, Johnson grass, cultivated oats, orchard grass, redtop, perennial rye grass, rice, sweet vernal grass, timothy, careless weed, pigweed, common cocklebur, sorrel dock, goldenrod, kochia, lamb's quarters, marigold, nettle, pigwood, English plantain, giant ragweed, short ragweed, western ragweed, Russian thistle, sagebrush, Scotch broom, or sheep sorrel.

* * * * *